(12) United States Patent
Higgins

(10) Patent No.: US 11,013,904 B2
(45) Date of Patent: May 25, 2021

(54) INTRAVASCULAR PUMP WITH PROXIMAL AND DISTAL PRESSURE OR FLOW SENSORS AND DISTAL SENSOR TRACKING

(71) Applicant: Cardiovascular Systems, Inc., St. Paul, MN (US)

(72) Inventor: Joseph P. Higgins, Minnetonka, MN (US)

(73) Assignee: Cardiovascular Systems, Inc., St. Paul, MN (US)

( * ) Notice: Subject to any disclaimer, the term of this patent is extended or adjusted under 35 U.S.C. 154(b) by 0 days.

(21) Appl. No.: 16/524,548

(22) Filed: Jul. 29, 2019

(65) Prior Publication Data

US 2020/0030510 A1     Jan. 30, 2020

Related U.S. Application Data

(60) Provisional application No. 62/711,766, filed on Jul. 30, 2018.

(51) Int. Cl.
| | |
|---|---|
| *A61M 60/135* | (2021.01) |
| *A61M 60/148* | (2021.01) |
| *A61M 60/205* | (2021.01) |
| *A61M 60/40* | (2021.01) |
| *A61M 60/50* | (2021.01) |
| *A61M 60/857* | (2021.01) |

(52) U.S. Cl.
CPC ........ *A61M 60/135* (2021.01); *A61M 60/148* (2021.01); *A61M 60/205* (2021.01); *A61M 60/40* (2021.01); *A61M 60/50* (2021.01); *A61M 60/857* (2021.01)

(58) Field of Classification Search
CPC .... A61M 1/125; A61M 1/1024; A61M 1/122; A61M 1/1008; A61M 1/1029; A61M 1/1086
See application file for complete search history.

(56) References Cited

U.S. PATENT DOCUMENTS

| | | | |
|---|---|---|---|
| 4,969,865 A * | 11/1990 | Hwang | F04D 3/00 415/900 |
| 2004/0191116 A1 | 9/2004 | Jarvik et al. | |
| 2009/0112312 A1* | 4/2009 | LaRose | A61M 1/122 623/3.13 |
| 2015/0141842 A1* | 5/2015 | Spanier | A61B 5/02154 600/478 |
| 2015/0297813 A1 | 10/2015 | Korakianitis et al. | |
| 2017/0021070 A1 | 1/2017 | Petersen | |

OTHER PUBLICATIONS

International Search Report and Written Opinion of the International Searching Authority, or the Declaration, dated Oct. 2, 2019, in PCT Application No. PCT/US19/44069, filed Jul. 30, 2019.

* cited by examiner

*Primary Examiner* — Catherine M Voorhees
*Assistant Examiner* — Roland Dinga
(74) *Attorney, Agent, or Firm* — Barnes & Thornburg LLP; Jeffrey R. Stone

(57) ABSTRACT

The present invention provides an intravascular blood pump comprising a pump assembly without a flow inducer or diffuser, and proximal and distal flow rate or pressure sensors, wherein the distal flow rate or pressure sensor may be tracked distal to the impeller after placement of the blood pump within the patient's vasculature.

11 Claims, 6 Drawing Sheets

INTRAVASCULAR PUMP WITH PROXIMAL AND DISTAL PRESSURE OR FLOW SENSORS AND DISTAL SENSOR TRACKING

CROSS-REFERENCE TO RELATED APPLICATIONS

This application claims priority to U.S. Provisional Patent Application No. 62/711,766, filed Jul. 30, 2018 and titled INTRAVASCULAR PUMP WITH DIRECT FLOW RATE PRESSURE SENSORS WITH DISTAL SENSOR TRACKING the contents of which is hereby incorporated by reference in its entirety.

STATEMENT REGARDING FEDERALLY SPONSORED RESEARCH OR DEVELOPMENT

Not Applicable

BACKGROUND OF THE INVENTION

Field of the Invention

The invention relates to an intravascular blood pump with an expandable and collapsible inlet region.

Description of the Related Art

With reference to FIG. 1, the human heart comprises four chambers and four heart valves that assist in the forward (antegrade) flow of blood through the heart. The chambers include the left atrium, left ventricle, right atrium and right ventricle. The four heart valves include the mitral valve, the tricuspid valve, the aortic valve and the pulmonary valve.

The mitral valve is located between the left atrium and left ventricle and helps control the flow of blood from the left atrium to the left ventricle by acting as a one-way valve to prevent backflow into the left atrium. Similarly, the tricuspid valve is located between the right atrium and the right ventricle, while the aortic valve and the pulmonary valve are semilunar valves located in arteries flowing blood away from the heart. The valves are all one-way valves, with leaflets that open to allow forward (antegrade) blood flow. The normally functioning valve leaflets close under the pressure exerted by reverse blood to prevent backflow (retrograde) of the blood.

Thus, as illustrated, the general blood flow comprises deoxygenated blood returning from the body where it is received by the right atrium via the superior and inferior vena cava and is, in turn, pumped into the right ventricle, a process controlled by the tricuspid valve. The right ventricle functions to pump the deoxygenated blood to the lungs via the pulmonary arteries, where the blood is reoxygenated and returned to the left atrium via the pulmonary veins.

Heart disease is a health problem with a high mortality rate. The use of temporary mechanical blood pump devices are used on an increasingly frequent basis to provide short-term acute support during surgery or as temporary bridging support to help a patient survive a crisis. These temporary blood pumps have developed and evolved over the years to supplement the pumping action of the heart on a short-term basis and supplement blood flow as either left or right ventricular assist devices, with the left ventricular assist device ("LVAD") currently the most commonly used device.

Known temporary LVAD devices generally are delivered percutaneously, e.g., through the femoral artery, to locate or position the LVAD inlet in the patient's left ventricle and the outlet in the patient's ascending aorta with the body of the device disposed across the aortic valve. As the skilled artisan will understand, an incision may be made below the patient's groin to enable access to the patient's femoral artery. The physician may then translate guide wire, followed by a catheter or delivery sheath, through the femoral artery and descending aorta until reaching the ascending aorta. The LVAD with attached rotational drive shaft may then be translated through the delivery catheter or sheath lumen, leaving a proximal end of the drive shaft exposed outside of the patient and coupled with a prime mover such as an electric motor or the equivalent for rotating and controlling the rotational speed of the drive shaft and associated LVAD impeller.

Temporary axial flow blood pumps consist generally of two types: (1) those that are powered by a motor integrated into the device that is connected with the pump's impeller (see U.S. Pat. Nos. 5,147,388 and 5,275,580); and (2) those that are powered by an external motor that provides rotational torque to a drive shaft which is, in turn, connected to the pump's impeller (see U.S. Pat. No. 4,625,712 to Wampler and U.S. Pat. No. 5,112,349 to Summers, each hereby incorporated by reference in their entirety).

Known temporary ventricle assist devices ("VAD"), including LVAD and RVAD (right ventricular assist) devices, whether with integrated motor or an external motor, generally comprise the following elements mounted within a housing, listed in order from the inflow end to the outflow end: an inflow aperture(s); a flow inducer, known in the art as component that directs flow into the impeller from the inflow apertures or inlet; a rotational impeller; and a flow diffuser and/or outflow structure known in the art as functioning to straighten or redirecting the rotational flow created by the rotational impeller into axial flow; and an outflow aperture(s) as shown in the exemplary prior art pump and/or impeller assembly cross sectional and cutaway view of FIG. 2.

In FIG. 2, the known device 2 is oriented with the inflow end (distal end) on the left side of the drawing and the outflow end (proximal) on the right side, so that the incoming blood flow in the ventricle enters the device housing through the inflow aperture(s) (not shown), flows through the defined by the surrounding housing 14, ultimately entering the impeller/pump assembly 4. There, the incoming blood encounters the flow inducer 6 before being urged forward by the rotating impeller 8. The blood flow may then be modified by a flow diffuser 9 and exits into the aorta via the housing's outflow aperture(s) 10.

Known VAD or LVAD devices further comprise a delivery configuration and a functional or working configuration, with the delivery configuration having a lower profile or smaller diameter than the functional or working configuration to, inter alia, facilitate atraumatic delivery through a delivery sheath. Stated differently, through various means the housing of the VAD or LVAD, and/or the blades of the impeller, may expand to achieve the functional or working configuration and collapse to achieve the delivery configuration. However, known devices collapse and expand the impeller blades and/or the housing wherein the collapsible and expandable housing surrounds at least a portion of the impeller in order to enable moving between an expanded or working configuration and/or require an integrated motor proximate the impeller. See, e.g., U.S. Pat. Nos. 7,027,875; 7,927,068; and 8,992,163.

Known LVAD devices will typically comprise an angled housing to accommodate the aortic arch, the angle or bend generally in the range of 135 degrees.

LVAD devices with integrated motors within the housing must be small enough to allow atraumatic intravascular translation and positioning within the heart. Though various means are known to collapse portions of the device while within the catheter or delivery sheath, including the housing and/or the impeller or parts thereof such as the blades, the size of the collapsed device may be limited by the integrated motor.

In addition, the known LVAD devices comprise a delivery configuration wherein the housing and/or impeller, e.g., the blades on the impeller, may be reduced in diameter and, when delivered distally from the delivery catheter or sheath, the collapsed elements are enabled to expand. These devices are limited in several respects. First, the collapsing and expanding comprises at least a portion of the housing that is occupied by the impeller. Second, the inflow region of the housing, that is the region distal to the rotational impeller and the stationary inducer or flow straightener, comprises an area of opportunity to optimize blood flow through the cannula or housing. Known LVAD or VAD devices do not take advantage of this opportunity. Third, known LVAD or VAD devices comprise a flow inducer or flow straightener encountered by blood upon entry into the pump which can contribute to, inter alia, thrombosis and/or hemolysis. Fourth, reducing crossing profile of the VAD or LVAD device is critical for reasons discussed herein, a design requirement made more difficult by the need to extend electric leads across or along the housing of the device, wherein the electrical leads may be used for, e.g., powering and/or communicating with a motor or sensor(s) or other operational powered element. In this connection, electric leads require profile reduction to keep the crossing profile as low as possible, as well as insulation and/or spacing between adjacent leads where such insulation and/or spacing is necessary or desired. Further, a direct method to measure pressure and/or flow rate is desired.

Various embodiments of the present invention address these, inter alia, issues.

The figures and the detailed description which follow more particularly exemplify these and other embodiments of the invention.

DETAILED DESCRIPTION OF THE INVENTION

Generally, various embodiments of the present invention are directed to mechanical assist devices for pumping blood in a patient. Improved temporary LVAD or VAD blood pumps are described herein that are delivered percutaneously and intravascularly.

Figure 3:
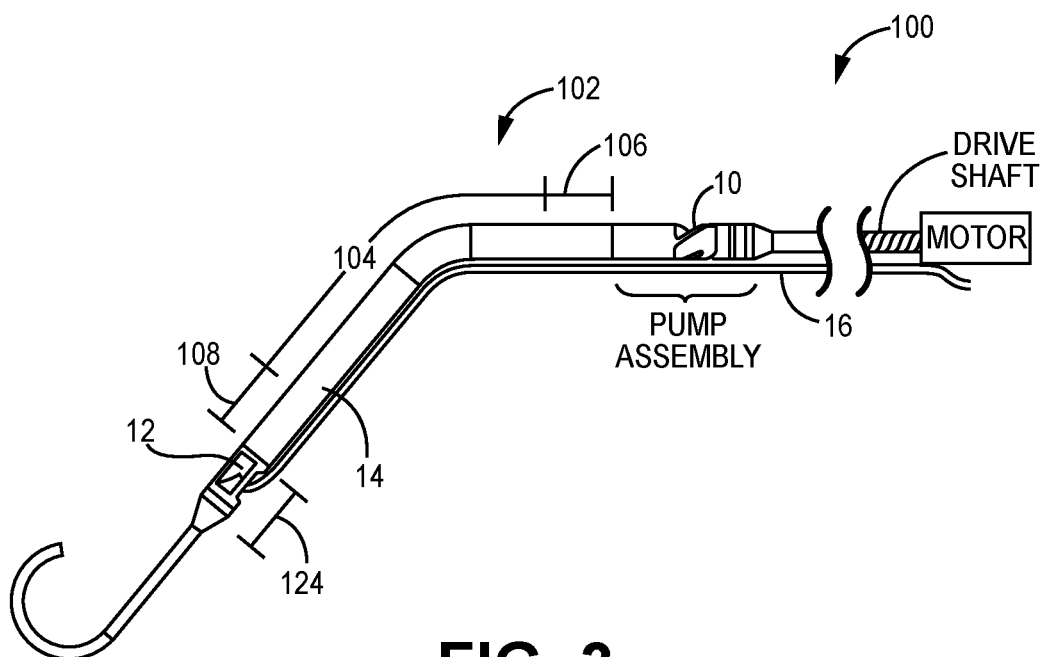
FIG. 3 is a side cutaway view of one embodiment of the present invention.

Referring now to FIG. 3, an exemplary LVAD blood pump 100 is illustrated, with inflow apertures 12 on the left side of the illustration and outflow apertures 10 on the right side of the device. The motor is shown as located on the proximal end of the device outside the patient's body and connected with a rotational drive shaft that is, in turn, connected with the impeller or rotor 8 or pump assembly. However, as is well known in the art, the motor may be located within the housing of the device itself, wherein the motor is typically mounted on the proximal side of the rotor 8 or impeller or pump assembly. Either of these configurations may be used together with various embodiments of the present invention as described herein.

The entire length of outer housing 14 is shown as comprising a relatively constant diameter from the inlet or inflow apertures 12 to the outlet or outflow apertures 10. Guide wire 16 is positioned alongside the exterior of the device until reaching the inlet apertures 12 where it enters the lumen of cannula C and extends distally therefrom as shown. Thus, the guide wire 16 does not pass through the impeller or rotor 8 or pump assembly. The configuration shown in FIG. 3 may comprise a delivery configuration with an expandable region 102 compressed within an introducer or delivery sheath or catheter 200.

With reference generally to the Figures, device 100 may comprise an expandable region 102 that may be located distal to the impeller or rotor or pump assembly, such that the housing diameter surrounding the impeller or rotor or pump assembly does not change diameter during delivery or during rotation. Stated differently, a proximal non-expandable region 122 may be provided and comprises at least the impeller or rotor or pump assembly and the housing surrounding that assembly does not expand or contract appreciably but may be flexible. Further, a distal non-expandable region 124 may also be provided comprising at least the inlet region including at least the inlet apertures 12. Thus, the expandable region 102 comprises a proximal end and a distal end. The proximal end of the expandable region 102 abuts or is adjacent to a distal end of the proximal non-expandable region 122 while the distal end of the expandable region 102 abuts or is adjacent to a proximal end of the distal non-expandable region 124. The housing H surrounding the non-expandable region(s) 122, 124 may, however, be flexible or pliable, but they are not disposed to a biased expansion.

Alternatively, the housing H of device 100 in FIG. 3 may be non-expandable.

Figure 4:
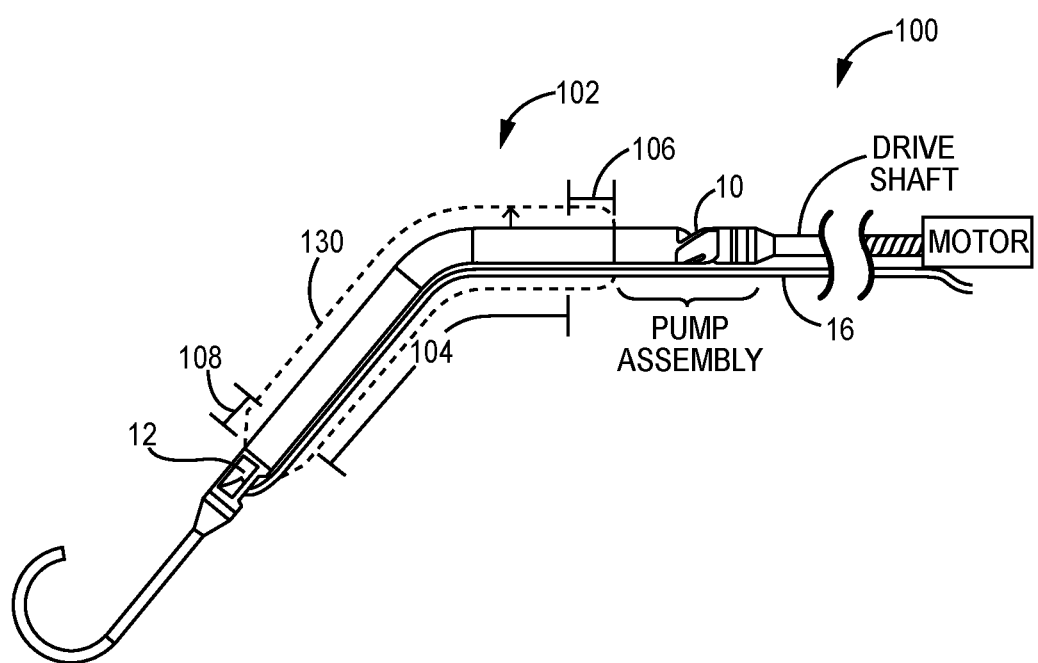
FIG. 4 is a side cutaway view of one embodiment of the present invention.

FIG. 4 illustrates an expandable embodiment of device 100 and in dashed lines the change in diameter to/from a collapsed, deformed expandable region to an exemplary expanded undeformed expandable region, extending distally from a point distal to the end of the impeller, rotor and/or pump assembly along the hollow cannula to a point just proximal of the inlet apertures. The expandable region 102 may expand to a maximum undeformed diameter within the range of 12-20 Fr, more preferably between 16-20 Fr. In contrast, the unexpanded region remains at a substantially fixed diameter within the range of 9 to 12 Fr.

With continued reference to FIGS. 3 and 4, and the remaining Figures generally, the device 100 may comprise an expandable region 102 that may be, either partially or completely, biased to the expanded configuration and, therefore, comprise a material or structure that facilitates expansion and may be biased to expand. Exemplary construction of the expandable region 102 may comprise a support structure 130 that is surrounded by an outer material, e.g., a jacket or coating or sleeve comprised of a plastic or polymeric material that accommodates an expansion of the underlying support structure as is known in the art. The support structure 130 may be formed of a shape memory material, for example Nitinol or similar. Other materials may comprise gold, tantalum, stainless steel, metal alloys, aerospace alloys and/or polymers including polymers that expand and contract upon exposure to relative heat and cold. In other cases, at least a portion of the expandable region 102, e.g., a central expandable section 104 discussed infra, may comprise a polymeric or other material sleeve that is configured to allow and/or accommodate expansion and collapsing and a support structure 130 may be omitted. FIG. 4 provides a rotational drive shaft connected with the impeller assembly and is, in turn, connected with a prime mover such as an electric motor that is located outside the patient's body. It will be understood, however, that the various embodiments of the inventions discussed herein may also be used in combination with blood pumps comprising motors integrated therein, i.e., no external motor. Further, as discussed above, device 100 may comprise an expandable housing H or region 102 or may be non-expandable.

In many of the embodiments described herein, the expandable region 102 may comprise a single expandable region, without need or reason to distinguish between a proximal transition section, central expandable section and/or distal transition section.

Generally, the expandable region 102 of the present invention may comprise a support structure 130 surrounded by a polymer coating or jacket that adapts to expansion and collapsing of the expandable region 102.

Further, the support structure 130 may comprise an expandable stent-like structure formed of a series of cells formed from interacting and/or interconnected wires and/or struts and that enable collapsing and biased expansion of a structure, e.g., a stent, as is known in the art. For example, see U.S. Pat. No. 5,776,183 to Kanesaka; U.S. Pat. No. 5,019,090 to Pinchuk; U.S. Pat. No. 5,161,547 to Tower; U.S. Pat. No. 4,950,227 to Savin; U.S. Pat. No. 5,314,472 to Fontaine; U.S. Pat. Nos. 4,886,062 and 4,969,458 to Wiktor; and U.S. Pat. No. 4,856,516 to Hillstead, the disclosures of each of which are hereby incorporated in their entirety by reference.

The expandable region 102 described herein is merely exemplary and not limiting in any regard. As such, any expandable housing H of a blood pump device 100 is readily adaptable to the various embodiments of the present invention relating to insulation and/or spacing and/or profile reduction or integration of electrical leads or conductors E within or along the blood pump housing. Expandable region 102 may also comprise a single region capable of expansion and collapse.

Figure 5:
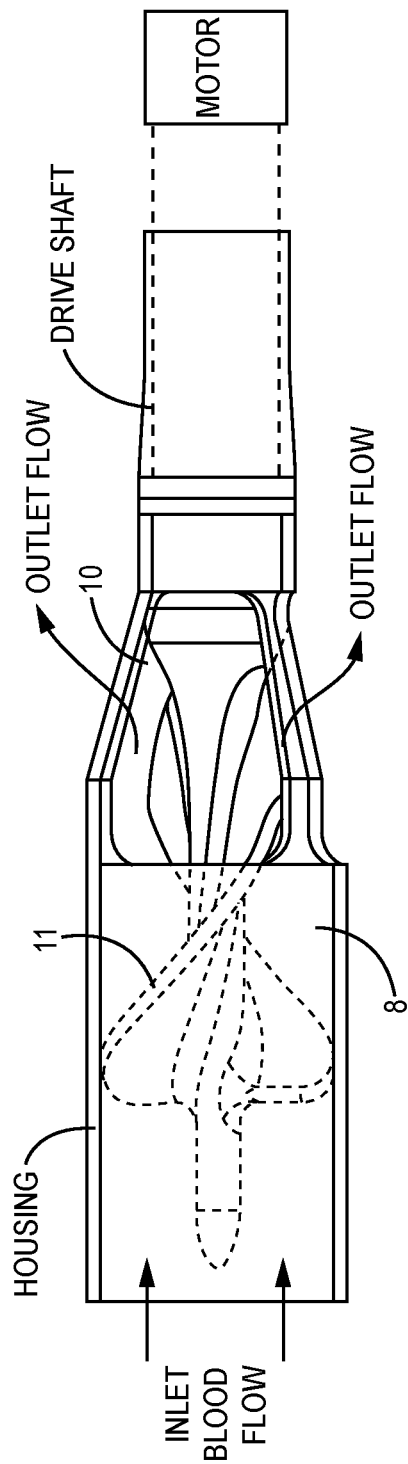
FIG. 5 is a side cutaway of one embodiment of the present invention.

Turning now to FIG. 5, an exemplary pump assembly or impeller assembly 200 is illustrated.

Figure 1:
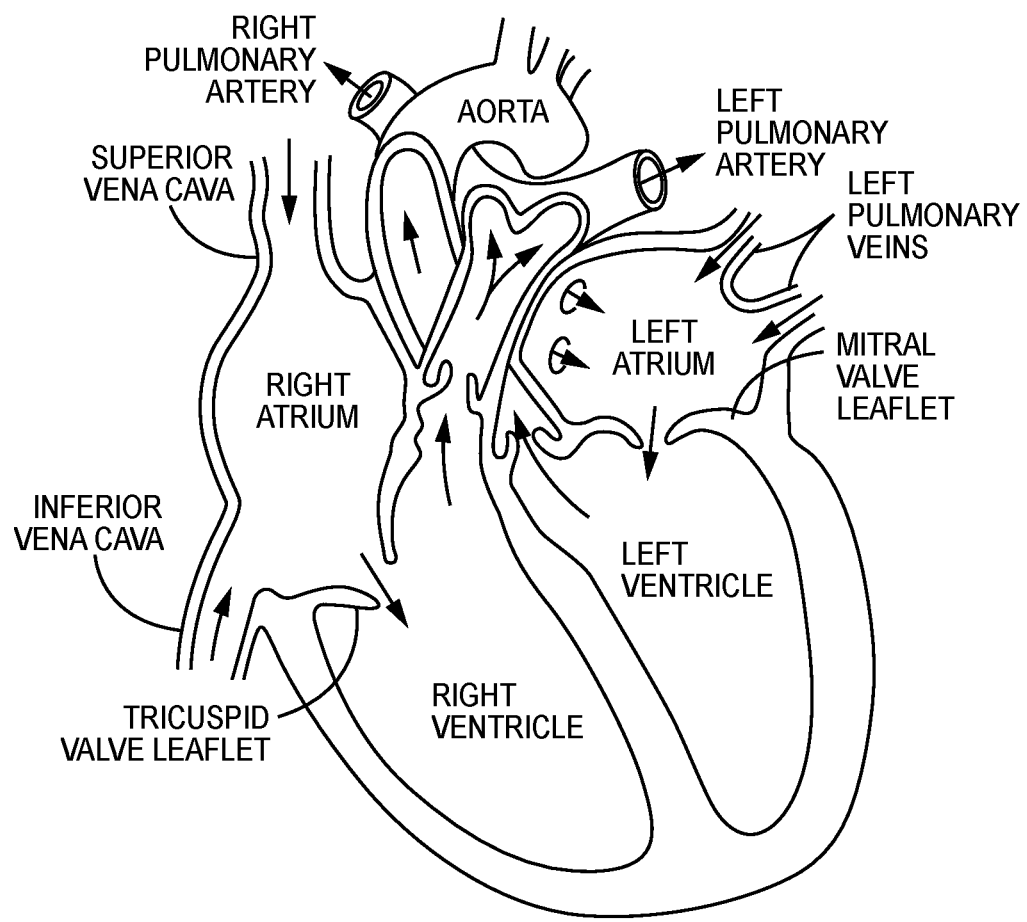
FIG. 1 is a cutaway view of the human heart.
Figure 2:
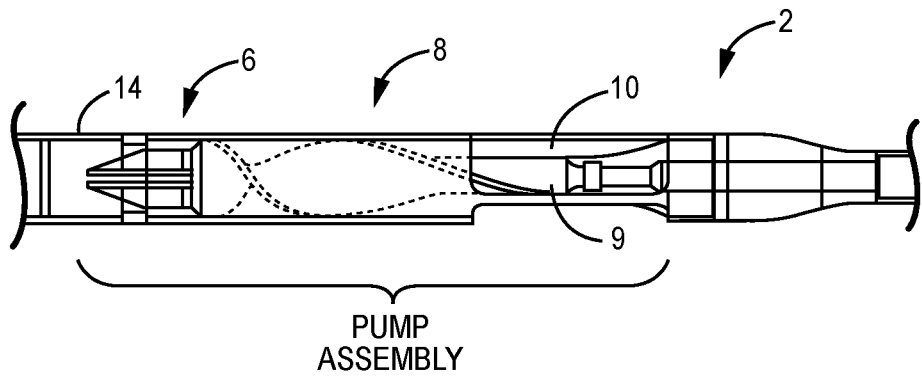
FIG. 2 is a cross-sectional view of a prior art device.

Initially, in contrast to the known impeller assembly shown in FIG. 2 which comprises a flow inducer 6 and flow diffuser 9, the exemplary pump or impeller assembly of FIG. 5 completely eliminates the flow inducer 6 and the flow diffuser 9 of the impeller assembly found in known pumps as shown in FIG. 2. Applicant has found that the inducer 6 and/or diffuser 9 are not needed for effective control or manipulation of the incoming blood flow and that the additional stationary surface area and interconnections between at least the inducer 6 and the distal end of the rotating impeller 8 provide increased risk of thrombosis. Thus, the blood is induced to flow through the cannula of by actuating the pump or impeller assembly to rotate at a predetermined speed, without aid or requirement of a flow inducer. The blood thus flows directly to the rotating impeller 8 comprising blades 11 and is urged out of the cannula or lumen of the device at outlet apertures 10 by the rotating impeller blades 11, without aid or requirement of a flow diffuser or straightener.

Figure 6A:
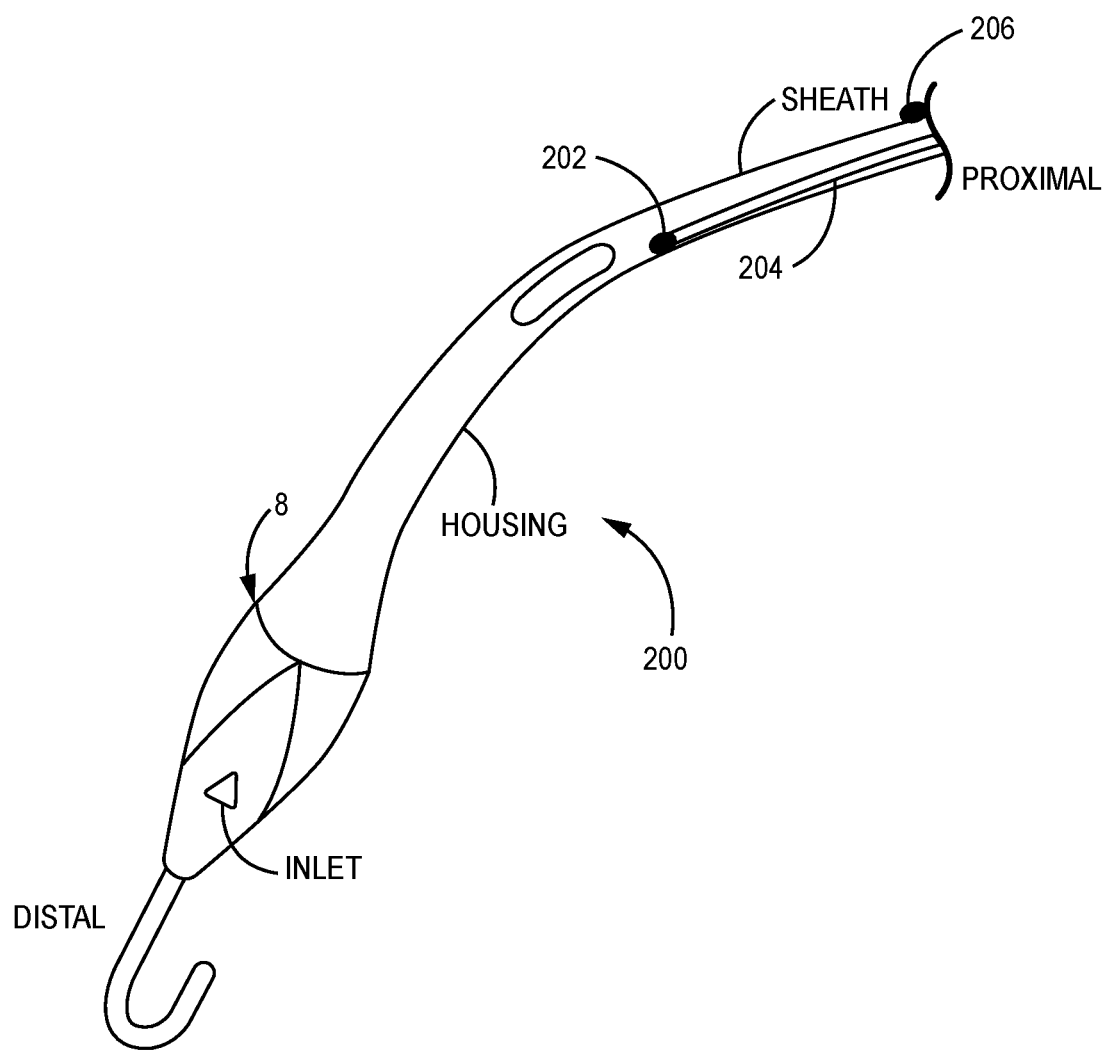
FIG. 6A is a side cutaway of one embodiment of the present invention.
Figure 6B:
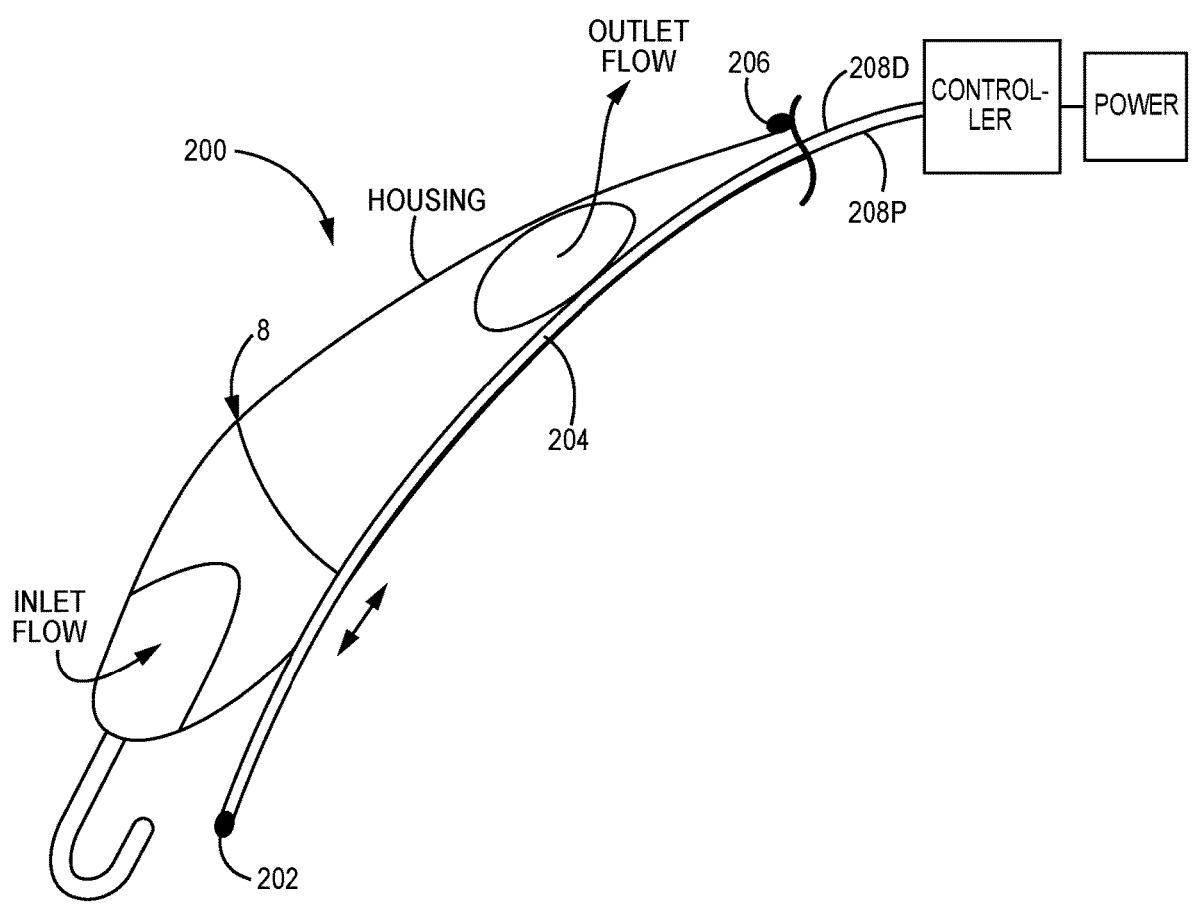
FIG. 6B is a side cutaway of one embodiment of the present invention.

Turning now to FIGS. 6A and 6B, a system 200 is provided for directly measuring flow rate. Currently known solutions provide an aortic pressure measurement through a pressure sensor located proximal to the impeller pump housing assembly. Output flow is calculated in these known devices based on the aortic pressure, the impeller rotational speed and the motor current. Therefore, provision of a pressure sensor within the left ventricle on a positioned blood pump device will allow for LVDP pressure sensing and measurement to determining offloading of the ventricle as well as the flow rate out of the left ventricle.

Running electrical leads along the device's housing is difficult as the known solutions require an increase in crossing profile. The present invention solves this problem.

The diameter of the subject lumen may be useful in the present invention to calculate flow rate based on pressure data. Thus, the direct flow rate measurement sensor devices may be provided within the blood pump at locations where the diameter is a fixed and known quantity, particularly in embodiments where the housing is not expandable. Alternatively, in the embodiments where the housing may be expandable, the diameter may be assessed by imaging or other known means during the LVAD procedure.

As shown in FIG. 6, at least one distal sensor 202, which may comprise a pressure sensor or an ultrasonic flow meter, may be initially disposed within or along the blood pump device at a first location $L_1$ proximal to the impeller, then translated distally with a push wire 204 or the equivalent to a second location $L_2$ within the patient's left ventricle, wherein the second location $L_2$ is distal to the impeller, when the blood pump device is operationally positioned.

The translation or tracking of the distal pressure sensor 202 from the first location to the second location is achieved by manipulation performed by the operator, by means known in the art, e.g., using a push wire 204 or the equivalent to move the distal sensor 202 to its second location $L_2$ within the left ventricle. Alternatively, in the case of a blood pump comprising an expandable inlet using expansion means and structure described above, the distal sensor 202 may be operatively connected with the expandable inlet. In this embodiment, the collapsed inlet (during insertion through sheath) comprises a smaller diameter than when the inlet expands (working configuration). Thus, the distal sensor 202 may be operatively attached to the inlet so that as the inlet moves from a collapsed position to the expanded position, the distal sensor is pulled distally to a point within the left ventricle.

At least one proximal pressure or flow rate sensor 206 may be mounted within the blood pump sheath, a region that is generally located within the patient's aorta when operationally positioned.

The electrical lead 208P, 208D for both sensors 206, 204 may run from an externally located power source and the controller through the sheath as shown, along the lumen created outside the drive shaft when the drive shaft is translated through the sheath. Thus, sensors 202, 204 are in operative connection and communication with the external power source and the controller and adapted to transmit pressure or flow rate data to the controller.

The controller comprises programmed instructions and a processor for executing the programmed instructions which, when executed produce real time sensor readings based on the pressure data received from the sensors 202, 204. The real time sensor readings may be communicated to a display to allow the operator to ensure that the pressure and/or flow rate produced during operation of the rotating impeller 8 is within the optimal range.

This method and system for measuring flow rate is improved as it is a direct measurement of flow rate and not an indirect methodology as in known systems that derive estimates for flow rate based on a measured pressure and motor speed.

The description of the invention and is as set forth herein is illustrative and is not intended to limit the scope of the invention. Features of various embodiments may be combined with other embodiments within the contemplation of this invention. Variations and modifications of the embodiments disclosed herein are possible and practical alternatives to and equivalents of the various elements of the embodiments would be understood to those of ordinary skill in the art upon study of this patent document. These and other variations and modifications of the embodiments disclosed herein may be made without departing from the scope and spirit of the invention.

The invention claimed is:

1. A blood pump assembly having an inlet and inlet housing and an outlet and adapted for positioning within a patient's aorta and left ventricle, comprising:
    a motor in operative rotational engagement with an impeller assembly, the impeller assembly comprising an impeller housing, an impeller within the impeller housing, the impeller comprising an impeller hub and blades in operative engagement with the impeller hub, wherein the impeller assembly does not include a flow inducer or a flow diffuser;
    a sheath operatively connected with the impeller housing and wherein the impeller assembly does not include a flow inducer or a flow diffuser;
    a flexible drive shaft translated through the sheath and in operative connection with a proximal end of the impeller and the motor, wherein a lumen is provided between the flexible drive shaft and the sheath when the drive shaft is translated therethrough;
    a proximal pressure or flow rate sensor mounted along the sheath at a location proximal to the impeller, wherein when positioned for operation the proximal pressure or flow rate sensor is within the patient's aorta; and
    a distal pressure or flow rate sensor located at a first position that is proximal to the impeller, wherein the distal pressure or flow rate sensor is adapted to be subsequently translated to a second location within the patient's left ventricle and distal to the location of the impeller;
    an external power source;
    an external controller in operative connection with the external power source;
    a first electric lead in operative connection with the proximal pressure or flow rate sensor, the external power source and the external controller, the first electric lead translated along the lumen between the drive shaft and the sheath; and
    a second electric lead in operative connection with the distal pressure or flow rate sensor, the external power source and the external controller, the second electric lead translated through the lumen between the drive shaft and the sheath.

2. The blood pump assembly of claim 1, further comprising the controller adapted to calculate the pressure or flow rate of the blood pump based on input received from the first and second pressure or flow rate sensors.

3. The blood pump assembly of claim 2, further comprising a push wire operatively connected with the distal pressure or flow rate sensor and adapted to translate the distal pressure or flow rate sensor to the second location.

4. A blood pump assembly having an inlet and an outlet adapted for positioning within a patient's aorta and left ventricle, comprising:
    a motor in operative rotational engagement with an impeller assembly, the impeller assembly comprising an impeller housing, an impeller within the impeller housing, the impeller comprising an impeller hub and blades in operative engagement with the impeller hub;
    a sheath operatively connected with the impeller housing, wherein the impeller assembly does not include a flow inducer or a flow diffuser;
    a flexible drive shaft translated through the sheath and in operative connection with a proximal end of the impeller and the motor;
    a proximal pressure or flow rate sensor mounted along the sheath at a location proximal to the impeller, wherein when positioned for operation the proximal pressure or flow rate sensor is within the patient's aorta; and
    a distal pressure or flow rate sensor located at a first position that is proximal to the impeller, wherein the distal pressure or flow rate sensor is adapted to be subsequently translated to a second location within the patient's left ventricle at a location that is distal to the impeller;
    an external power source;
    an external controller in operative connection with the external power source;
    a first electric lead in operative connection with the proximal pressure or flow rate sensor, the external power source and the external controller, the first electric lead translated along a lumen between the drive shaft and the sheath; and
    a second electric lead in operative connection with the distal pressure or flow rate sensor, the external power source and the external controller, the second electric lead translated through the lumen between the drive shaft and the sheath.

5. The blood pump assembly of claim 4, wherein the controller is adapted to calculate the flow rate of the blood pump based on input received from the first and second pressure or flow rate sensors.

6. The blood pump assembly of claim 5, further comprising a push wire operatively connected with the distal pressure or flow rate sensor and adapted to translate the distal pressure or flow rate sensor to the second location.

7. A blood pump having a motor-powered rotational impeller, an inlet and inlet housing and an outlet and adapted for positioning within a patient's aorta and left ventricle, comprising:
    a proximal pressure or flow rate sensor mounted along a sheath at a location proximal to the impeller, wherein when positioned for operation the proximal pressure or flow rate sensor is within the patient's aorta; and
    a distal pressure or flow rate sensor located at a first position that is proximal to the impeller, wherein the distal pressure or flow rate sensor is adapted to be subsequently translated to a second location within the patient's left ventricle at a location that is distal to the impeller when the blood pump is positioned;
    an external power source;

an external controller in operative connection with an external power source;

a first electric lead in operative connection with the proximal pressure or flow rate sensor, the external power source and the external controller; and a second electric lead in operative connection with the distal pressure or flow rate sensor, the external power source and the external controller.

8. The blood pump assembly of claim 7, wherein the external controller is adapted to calculate the flow rate of the blood pump based on input received from the first and second pressure or flow rate sensors.

9. The blood pump assembly of claim 8, further comprising a push wire operatively connected with the distal pressure or flow rate sensor and adapted to translate the distal pressure or flow rate sensor to the second location.

10. A method for directly measuring pressure across a blood pump that is positioned within the aorta and left ventricle of a patient during rotation of the pump's impeller, comprising:

providing a sheath operatively connected with the impeller housing and wherein the impeller assembly does not include a flow inducer or a flow diffuser;

providing a proximal pressure or flow rate sensor fixed to the sheath proximal to the positioned blood pump's impeller;

providing a distal pressure or flow rate sensor that, after the blood pump is positioned, is translated to a location that is distal to the positioned blood pump's impeller;

providing an external controller operatively connected with the proximal and distal pressure sensors;

operating the positioned blood pump's impeller to generate blood flow;

obtaining pressure or flow rate signals from the proximal and distal pressure or flow rate sensors at the external controller; and determining pressure or flow rate based on the obtained pressure or flow rate signals.

11. The method of claim 10, further comprising providing an operatively connected display and displaying the obtained pressure or flow rate signals on the display.

\* \* \* \* \*